United States Patent [19]

Krohn et al.

[11] 4,086,341
[45] Apr. 25, 1978

[54] CEPHALOSPORIN DERIVATIVES

[75] Inventors: Wolfgang Krohn, Leverkusen; Karl Georg Metzger; Michael Preiss, both of Wuppertal; Michael Walkowiak, Cologne, all of Germany

[73] Assignee: Bayer Aktiengesellschaft, Germany

[21] Appl. No.: 707,853

[22] Filed: Jul. 22, 1976

Related U.S. Application Data

[62] Division of Ser. No. 602,969, Aug. 8, 1975, Pat. No. 4,012,518.

[30] Foreign Application Priority Data

Aug. 22, 1974 Germany ............................. 2440268

[51] Int. Cl.$^2$ ................. C07D 501/20; A61K 31/545
[52] U.S. Cl. ...................................... 424/246; 544/26; 260/239.1; 544/30; 544/16
[58] Field of Search .................... 260/243 C; 424/246; 544/26, 27

[56] References Cited

U.S. PATENT DOCUMENTS 3,996,208  12/1976  Fechtig et al. ................... 260/243 C Primary Examiner—Nicholas S. Rizzo
Attorney, Agent, or Firm—Jacobs & Jacobs

[57] ABSTRACT

Penicillin and cephalosporin derivatives characterized by the presence of a nitroalkyl, nitrocycloalkyl, nitrophenylalkyl or nitroanilinoalkyl group in the side chain are antibacterial agents. The compounds, of which 6-(2-nitro-3,3-dimethylbutyrylamido)-penicillanic acid, 7-nitroacetamido-3-methyl-ceph-3-em-4-carboxylic acid, and 6-[D-α-(2-nitro-2-methylpropionylamido)phenylacetamido]-penicillanic acid are typical embodiments, are prepared by reacting 6-aminopenicillanic acid, 7-amino-cephalosporanic acid (or derivative thereof) or an α-substituted-α-aminoacetamido-penicillanic acid with an appropriate nitrated carboxylic acid or an equivalent nitrated acylating agent.

13 Claims, No Drawings

CEPHALOSPORIN DERIVATIVES

CROSS REFERENCE

This is a division of Ser. No. 602,969, filed Aug. 8, 1975, now U.S. Pat. No. 4,012,518 issued Mar. 15, 1977.

The present invention pertains to nitro-β-lactams and to processess for their preparation and use as antimicrobial agents and agents for promoting growth and feedstuff utilization in animals.

Acyl-substituted and arylacyl-substituted aminopenicillanic acids and cephalosporanic acids have proven very effective in the therapy of infections caused by Gram positive and Gram negative bacteria. Many however are active only if administered parenterally.

The present invention pertains to compounds of the formula:

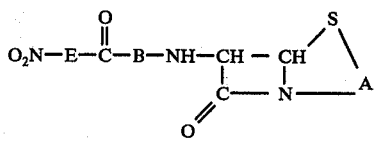
I wherein
$O_2N$—E is nitroalkyl of 1 to 6 carbon atoms, nitrocycloalkyl of 3 to 10 carbon atoms, nitrophenylalkyl of 7 to 13 carbon atoms or nitroanilinoalkyl of 7 to 13 carbon atoms;
B is a direct carbon-nitrogen bond or —NHC*HR$^1$-CO— in which the carbon atom designated by * constitutes a center of chirality and R$^1$ is phenyl, hydroxyphenyl or cyclohexa-1,4-dien-1-yl; and
A is

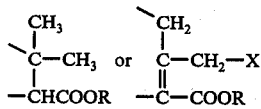

in which
R is hydrogen or

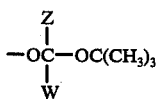

in which each of Z and W is independently hydrogen or lower alkyl; and
X is hydrogen, halo, hydroxy, azido, acetoxy, carbamoyl, 5-methyl-1,3,4-thiadiazol-2-yl-thio, 5-trifluoromethyl-1,3,4-thiadiazol-2-ylthio, or 1-methyl-1H-tetrazol-5-ylthio;
and the pharmaceutically acceptable salts of said lactams in which R is hydrogen.

The foregoing compounds of the invention (including hydrates and salts thereof) exhibit powerful antimicrobial, especially antibacterial, properties even on oral administration. Among the compounds of the invention which are salts therefore, those which are pharmaceutically acceptable are preferred. Surprisingly, these compounds also show a substantially greater antibacterial action against bacteria of the family of the Staphylococci, especially on oral administration, than do the known β-lactam antibiotics such as, for example, penicillin V.

In a first embodiment, the present invention pertains to compounds in which the nitro-β-lactam is of the formula:

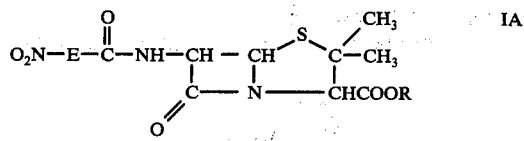
IA in which $O_2N$—E and R are as defined above. Particularly preferred are those compounds wherein R is hydrogen.

In a further embodiment, the nitro-β-lactam is of the formula:

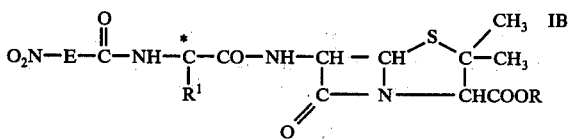
IB in which $O_2N$—E, R and R$^1$ are as defined above. In these compounds, the carbon atom designated by * constitutes a center of chirality by virtue of the asymmetric substitution. While both configurations are embraced, namely the R and S (corresponding to D and L respectively), the R configuration is preferred. The substituent R$^1$ when hydroxyphenyl includes the meta-, ortho- and para-hydroxyphenyl group, para being preferred. Phenyl is the preferred member of R$^1$ and R is preferably hydrogen.

In a further embodiment, the nitro-β-lactam is of the formula:

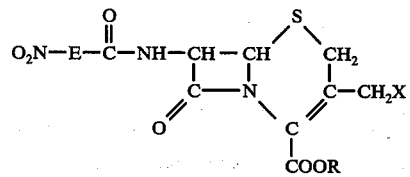
IC in which $O_2N$—E, R and X are as defined above. The groups embraced by X represent the known class of 3-substituents in cephalosporin compounds and hydrogen and acetoxy are preferred.

In a further embodiment, the invention pertains to compounds in which $O_2N$—E is nitroalkyl of 1 to 6 carbon atoms. The alkyl group can be branched or straight chained with the nitro group present on essentially any of its carbon atoms. Typical groups include nitromethyl, 1-nitroethyl, 2-nitroethyl, 1-nitropropyl, 2-nitropropyl, 3-nitropropyl, 2-nitroprop-2-yl, 1-nitroprop-2-yl, 1-nitrobutyl, 2-nitrobutyl, 3-nitrobutyl, 4-nitrobutyl, 1-nitrobut-2-yl, 2-nitrobut-2yl, 3-nitrobut-2-yl, 4-nitrobut-2-yl, 3-nitro-3-methylbutyl, 4-nitro-3,3-dimethylbutyl and the like.

In another embodiment, the invention pertains to compounds in which $O_2N$—E is nitrocycloalkyl of 7 to 13 carbon atoms, especially 3 to 7 and particularly 3, 5 or 6 carbon atoms. The cycloalkyl group can be monocyclic, bicyclic or tricyclic cycloalkyl and include nitrocyclopropyl, nitrocyclobutyl, nitrocyclopentyl, nitrocyclohexyl, nitrocycloheptyl, nitrobicyclo[2.2.1]- heptyl, nitrobicyclo[2.2.2]octyl, and nitroadamantyl. Nitrocyclohexyl is preferred. Preferably the nitro group is geminal to the carbonyl group through which $O_2N-E$ is joined.

In another embodiment, the invention pertains to compounds in which $O_2N-E$ is nitrophenylalkyl or nitroanilinoalkyl, each of 7 to 13 carbon atoms. In general these groups can be represented by the formula:

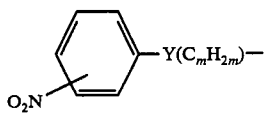

in which Y is a carbon-carbon bond or imino (—NH—), m has a value of 1 to 6, preferably 1 or 2, and the nitro group is on the ortho-, meta- or para-position, preferably para.

The substituents Z and W are hydrogen or lower alkyl, e.g. of 1 to 6 carbon atoms, preferably hydrogen.

The compounds of the present invention are prepared by (a) reacting an amino compound of the formula:

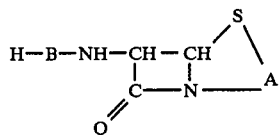

wherein B and A are as herein defined, or a derivative thereof in which the carboxylic acid group is chemically protected, with an acylating agent of the formula:

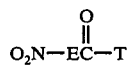

in which $O_2N-E$ is as defined above and

T is hydroxy, halo, azido, phenoxy, nitrophenoxy, dinitrophenoxy, monohalophenoxy, polyhalophenoxy, benzylthio, benztriazol-1-yloxy, 2,5-dioxopyrrolidin-1-yloxy, (lower alkoxy)carbonyloxy or imidazolide, (b) removing any protective group bound to said carboxylic acid group, (c) converting any nitro-β-lactam obtained as a free carboxylic acid into a corresponding pharmaceutically acceptable salt and/or (d) converting any nitro-β-lactam obtained as a salt into the corresponding free carboxylic acid compound.

A preferred protecting group for the compounds of Formula II is tri(lower alkyl)silyl, e.g. the trimethylsilyl ester of the compounds of Formula II. These can be prepared as described in German patent specification No. 1,159,449, U.S. Pat. No. 3,249,622 and British patent specification No. 964,449. In this method, the silylated derivatives are obtained by warming the compounds of Formula II in an inert solvent, for example hexane or benzene, with a light excess of a trialkylsilicon compound, for example hexamethyldisilazane, to 80° C under nitrogen for 4 to 5 hours, distilling off the excess silicon compound in vacuo and purifying and isolating the resulting silylated derivative according to customary methods. The distillate can also be reacted without isolation.

The starting materials of Formula II are, in general, known or are obtainable according to known methods. They are described, for example, in German published specification Nos. 1,931,722, 1,670,625, 1,795,188 and 1,795,292; U.S. Pat. Nos. 3,303,193, 3,352,858, 3,485,819 and 3,634,416; Japanese patent application No. 16,871/66; British patent specification Nos. 1,073,530 and 873,049; and Belgian Pat. No. 737,848. The following may be mentioned as examples: 6-aminopenicillanic acid, 6-(α-aminophenylacetamido)-penicillanic acid, 6-(α-amino-4-hydroxyphenylacetamido)-penicillanic acid, 6-(α-aminocyclohexa-1,4-dien-1-ylacetamido)-penicillanic acid, 7-(α-aminophenylacetamido)-3-methylceph-3-em-4-carboxylic acid, 7-(α-aminophenylacetamido)-3-hydroxymethylceph-3-em-4-carboxylic acid, 7-(α-aminophenylacetamido)-3-acetoxymethylceph-3-em-4-carboxylic acid, 7-(α-amino-4-hydroxyphenylacetamido)-3-methylceph-3-em-4-carboxylic acid, 7-(α-amino-4-hydroxyphenylacetamido)-3-hydroxymethylceph-3-em-4-carboxylic acid, 7-(α-aminocyclohexa-1,4-dien-1-ylacetamido)-3-acetoxymethylceph-3-em-4-carboxylic acid, 7-(α-aminocyclohexa-1,4-dien-1-ylacetamido)-3-methylceph-3-em-4-carboxylic acid, 7-(α-aminocyclohexa-1,4-dien-1-ylacetamido)-3-hydroxymethylceph-3-em-4-carboxylic acid, and the silylated derivatives (especially the derivatives containing trimethylsilyl groups).

The compounds of Formula II can be used in the form of any crystal form, hydrate form, salt, silyl compounds and easily splittable derivatives of the acid carboxyl group, such as, for example, easily splittable esters, amides or hydrazides, as starting materials for the present invention.

The compounds of Formula III are also known or can be readily prepared in accordance with conventional methods from known or easily obtainable nitrocarboxylic acids of the formula $O_2N-ECOOH$ wherein E is as defined above.

For example, the acid halides such as the acid chloride can be obtained through use of an agent which forms such halides upon reaction with an acid, for example thionyl chloride. Equally, however, compounds in which T is chlorine can be obtained from the hydrazides of these acids by reaction with chlorine. Those compounds of Formula III in which T is azide can be obtained from the corresponding compounds in which T is halogen, for example chlorine, by reaction with, for example, alkali metal azides. Those compounds of Formula III in which T is an unsubstituted or substituted phenyl radical or benzylthio radical can be obtained from the compounds in which T is halogen and the corresponding phenols or benzylmercaptan, or by direct reaction of the free acids with the corresponding phenols and benzylmercaptan. The following are examples of compounds of Formula III and their free acids, which can be used according to the invention, and the preparation of which is described in, for example, J. Org. Chem. 24, 1244 (1959), Bull, Chem. Soc. Japan 36, 1143 (1963) and C.A. 64, 80,236: nitroacetic acid, dipotassium nitroacetate, nitroacetic acid chloride, 2-nitropropionic acid chloride, 3-nitropropionic acid chloride, 2-nitro-2-methylpropionic acid chloride, 2-nitrobutyric acid chloride, 4-nitrobutyric acid chloride, 2-nitro-3,3-dimethylbutyric acid chloride, 4-nitro-4-methylvaleric acid chloride, 4-nitrophenylaminoacetic acid and 1-nitro-1-chlorocarbonylcyclohexane.

The reaction of the compounds of Formula II in the non-silylated form with those of Formula III is preferably carried out in a diluent, which may be water or any inert organic solvent or solvent mixture, which can also contain water. Organic solvents which are water-miscible, such as ketones, preferably lower dialkyl ketones ($C_1$–$C_8$), for example acetone and methyl ethyl ketone, cyclic ethers, for example tetrahydrofuran and dioxane, lower alkyl nitriles, for example acetonitrile, dimethylformamide, liquid alkanols, for example isopropanol, and/or dimethylsulphoxide can be used both in admixture with water and (individually or as mixtures) without addition of water.

If, because of the presence of water, pH measurement during the reaction according to the invention is feasible, the pH value of the reaction mixture is preferably kept at between 6.5 and 7.5, as by the addition of base or by use of buffered mixtures. The reaction however also can be carried out at other pH ranges, e.g. between 4.5 and 9.0 or at pH 2.0 to b 4.5. Furthermore it is possible to carry out the reaction in water-immiscible solvents, such as halogenated, especially chlorinated, hydrocarbons, for example chloroform or methylene chloride, with addition of organic amines, preferably lower alkylamines, such as triethylamine, diethylamine or N-ethylpiperidine. Similarly, the reaction can be carried out in mixtures of water and water-immiscible organic solvents, such as, for example, ether (diethyl ether), halogenated hydrocarbons, for example chloroform and methylene chloride, carbon disulfide, water-immiscible ketones, for example isobutyl methyl ketone, esters, for example ethyl acetate, and hydrocarbons, for example benzene, in which case it is desirable to stir the mixture vigorously and maintain the pH value at between about 4.5 to 9.0 or 2.0 to 3.0, by adding base or use of buffered solutions. The reaction can be carried out in water alone; i.e., in the absence of organic solvents and in the presence of an organic or inorganic base or with addition of bases. Any conventional organic or inorganic bases can be used. Examples of suitable bases are tertiary, aliphatic or aromatic amines, for example pyridine or lower trialkyl amines, for example triethylamine or secondary aliphatic or aromatic amines, for example dicyclohexylamine. Preferably the base is one which is difficult to acylate because of steric hindrance, but the number of usable bases is virtually unlimited. Suitable inorganic bases include alkali metal hydroxides and alkaline earth metal hydroxides, for example sodium hydroxide, potassium hydroxice and calcium hydroxide. The amount of base used is determined so as to maintain the preferred pH as discussed above. Where a pH measurement and adjustment is not carried out or is not feasible or meaningful (as in the absence of sufficient amounts of water in the diluent), about 1 to 5, especially about 2, molar equivalent amounts of base are added per molar equivalent of the starting compound of Formula II.

Conventional buffer mixtures can also be used, as for example phosphate buffers (sodium phosphate/phosphoric acid), acetate buffers (sodium acetate/acetic acid) and citrate buffers (sodium citrate/citric acid), and the mixing ratios required to maintain the desired pH values are easily determined.

If the compounds of Formula II are employed in their silylated form, an anhydrous aprotic solvent (or solvent mixture) is employed, preferably a halogenated lower hydrocarbon, such as methylene chloride or chloroform. The reaction of the silylated compounds can be carried out in the presence of an organic base, or without addition of base.

The reaction temperatures can be varied within a substantial range. In general, the reaction is carried out between about −40° and about +50° C, preferably between −30° and +20° C. The reaction can be carried out under normal pressure or under reduced or elevated pressure. In general, normal pressure is used. The reactants can be reacted with one another in, for example, equimolar amounts. However, it is often desirable to use one of the two reactants in excess to facilitate the purification, or preparation in a pure form, of the desired nitro-β-lactam and to increase the yield. The amounts of the reactants of Formulas II and III can be varied greatly without adverse consequences. For example, the reactants of Formula II can be employed in an excess of 0.1 to 0.3 mol equivalent and less decomposition of the reactants of Formula III in an aqueous solvent mixture is thus observed. An excess of a reactant of Formula II can easily be removed during working up of the reaction mixture as a result of their ready solubility in aqueous mineral acids. Isolation and purification of the new compounds are carried out in the customary manner generally known from penicillin and cephalosporin chemistry.

The free acids of Formula I can be prepared, for example, by acidifying a solution of the salts, for example of the sodium salts, with an inorganic or organic acid, for example with dilute hydrochloric acid or acetic acid. The free acids of Formula I can in turn be converted into the salts with non-toxic bases in the usual manner, for example by adding the base to an ethereal solution of the acid of Formula I.

The following may be mentioned as individual examples of new active compounds: 6-nitroacetamidopenicillanic acid, 7-nitroacetamido-3-methylceph-3-em-4-carboxylic acid, 6-[D-α-(nitroacetylamino)-phenylacetamido]-penicillanic acid, 6-(2-nitropropionylamido)-penicillanic acid, 6-(2-nitro-2-methylpropionylamido)-penicillanic acid, 7-(2-nitro-2-methylpropionylamido)-3-acetoxymethylceph-3-em-4-carboxylic acid, 6-[D-α-(2-nitro-2-methylpropionylamido)-phenylacetamido]-penicillanic acid, 6-(3-nitropropionylamido)-penicillanic acid, 7-(3-nitropropionylamido)-3-methylceph-3-em-4-carboxylic acid, 6-[D-α-(3-nitropropionylamido)phenylacetamido]-penicillanic acid, 6-(2-nitrobutyrylamido)-penicillanic acid, 7-(2-nitrobutyrylamido)-3-acetoxymethylceph-3-em-4-carboxylic acid, 6-[D-α-(2-nitrobutyrylamido)-phenylacetamido]-penicillanic acid, 7-(2-nitro-3,3-dimethylbutyrylamido)-3-acetoxymethylceph-3-em-4-carboxylic acid, 6-[D-α-(2-nitro-3,3-dimethylbutyrylamido)-phenylacetamido]-penicillanic acid, 6-(4-nitro-4-methylvaleroylamido)-penicillanic acid, 6-(4-nitrophenylaminoacetamide)-penicillanic acid, 7-(4-nitrophenylaminoacetamido)-3-acetoxymethylceph-3-em-4-carboxylic acid, 6-[D-α-(4-nitrophenylacetamido)phenylacetamido]-penicillanic acid, 6-[1-nitrocyclohex-1-ylcarbamido]-penicillanic acid and 7-[1-nitrocyclohex-1-ylcarbamido]-3-acetoxymethylceph-3-em-4-carboxylic acid.

Non-toxic, pharmaceutically acceptable salts of the compounds of Formula I are those of the carboxylic acid group, as for example the sodium, potassium, magnesium, calcium, aluminium, ammonium, si- and tri-lower alkylamines (preferably having $C_1$ to $C_4$ per alkyl group), procaine, dibenzylamine, N,N'-dibenzylethylenediamine, N-benzyl-β-phenylethylamine, N- methylmorpholine and N-ethylmorpholine, 1-ephenamine, dehydroabietylamine, N,N'-bis-dehydroabietylethylenediamine, N-lower alkylpiperidine and other amines customarily used in pharmaceutical chemistry, for example those which have also been used to form salts of known penicillins.

All crystal forms, salts and hydrate forms of the compounds of Formula I are suitable for use as anti-bacterial agents in the sense of the present invention. Thus, for example, the free acids and, for example, the sodium salts, either in an amorphous or in a crystalline form, and either anhydrous or in various hydrate forms, for example as the monohydrate, can be used in analogous fashion.

The present nitro-$\beta$-lactams and their salts possess low toxicity, are tolerated well, and exhibit a powerful antimicrobial activity. These properties permit their use as active compounds in medicine, and as compounds for preserving inorganic and organic materials, in particular organic materials of all kinds, for example polymers, lubricants, dyestuffs, fibres, leather, paper and timber, foodstuffs and water.

These nitro-$\beta$-lactams are active against a broad spectrum of micro-organisms including Gram negative and Gram positive bacteria and bacteria-like micro-organisms and they are therefore particularly suitable for the prophylaxis and chemotherapy of local and systemic infections caused by these pathogens, in both human and veterinary medicine, as for example infections of the respiratory tract and of the pharyngeal cavity, otitis, pharyngitis, pneumonia, peritonitis, pyelonephritis, cystitis, endocarditis, systemic infections, bronchitis, and arthritis of infectious origin.

The nitro-$\beta$-lactams are distinguished by powerful antibacterial effects and by oral resorbability. If desired, these compounds can be combined with aminoglycoside antibiotics such as, for example, gentamicin, kanamicin, amikacin or tobramicin, to broaden the spectrum of action or to boost the effect.

The antimicrobial activity of the compounds according to the invention can be conveniently observed in recognized in vitro and in vivo models. Thus white mice are infected intraperitoneally with *Staphylococcus aureus* 133 and the rate of survival between treated and untreated are observed for 5 days.

| Test Compound | Surviving animals, in % Days | | | |
|---|---|---|---|---|
| | 1 | 2 | 3 | 5 |
| Example No. 5 Dosage in units | | | | |
| a) 100 (subcutaneous) | 80 | 80 | 80 | 80 |
| b) 100 (oral) | 70 | 70 | 70 | 70 |
| Example No. 16 Dosage in units | | | | |
| a) 400 (subcutaneous) | 100 | 100 | 100 | 100 |
| b) 400 (oral) | 80 | 70 | 70 | 70 |
| untreated control | 10 | 0 | 0 | 0 |

Typical of the pathogens against which these compounds are active are:

Micrococcaceae, such as Staphylococci, for example *Staphylococcus aureus, Staph.epidermidis, Staph.aerogenes* and *Gaffkya tetragena* (Staph. = Staphylococcus);

Lactobacteriaceae, such as Streptococci, for example *Streptococcus pyogenes, α- and β-haemolysing Streptococci, non-(γ)-haemolysing Streptococci, Str. viridans, Str. faecalis* (Enterococci), *Str.agalactiae, Str.lactis, Str.equi, Str. anaerobis* and *Diplococcus pneumoniae* (Pneumococci) (Str. = Streptococcus);

Neisseriaceae, such as Neisseriae, for example *Neisseria gonorrhoeae* (Gonococci), *N.meningitidis* (Meningococci), *N.catarrhalis* and *N. flava* (N. = Neisseria);

Corynebacteriaceae, such as Corynebacteria, for example *Corynebacterium diphtheriae, C.pyogenes, D.diphtheroides, C.acnes, C.parvum, C.bovis, C.renale, C.ovis* and *C.murisepticum,* Listeria bacteria, for example *Listeria monocytogenes,* Erysipelothrix bacteria, for example *Erysipelothrix insidiosa,* and Kurthia bacteria, for example *Kurthia zopfii* (C. = Corynebacterium);

Enterobacteriaceae, such as Escherichiae bacteria of the Coli group, for example *Escherichia coli,* Enterobacter bacteria, for example *E.aerogenes* and *E.cloacae,* Klebsiella bacteria, for example *K.pneumoniae,* and *K.ozaenae,* Erwiniae, for example *Erwinia spec.,* Serratia, for example Serratia marcescens (E. = Enterobacter, K. = Klebsiella), Proteae bacteria from the Proteus group, Proteus, for example *Proteus vulgaris,* and Pr. mirabilis (Pr. = Proteus), Salmonelleae, Salmonella bacteria, for example *Salmonella paratyphi A* and *B, S.typhi, S.enteritidis, S.cholerae suis* and *S.typhimurium* (S. = Salmonella), Shigella bacteria, for example *Shigella dysenteriae, Sh.ambigua, Sh.flexneri, Sh.boydii* and *Sh.sonnei* (Sh. = Shigella);

Spirillaceae, such as Vibrio bacteria, for example *Vibrio cholerae, V.proteus* and *V.fetus* (V. = Vibrio), and Spirillum bacteria, for example Spirillum minus.

Spirochaetaceae, such as Borrelia bacteria, for example Borrelia recurrentia and B.vincentii (B. = Borrelia), Treponema bacteria, for example *Treponema pallidum, Tr. pertinue* and *Tr.carateum* (Tr. = Treponema), Leptospira bacteria, for example *Leptospira interrogans, Leptospira icterohaemorrhagiae, L.canicola, L.grippotyphosa, L.pomona, L.mitis* and *L.bovis* (L. = Leptospira).

Generally a suitable antibacterial effect is observed upon administration of from about 6 to about 800 mg/kg of body weight every 24 hours. A preferred dose range is 15 to 300 mg/kg. This can be given as a single daily dose, particularly in the case of long acting salts, or as several individual doses of from about 2 to about 300 mg/kg, divided over, for example, 3 administrations. However, it may be necessary to deviate from these guidelines and in particular to do so as a function of the age, condition and body weight of the subject to be treated, the nature and the severity of the illness, the nature of the preparation and route of administration, the response to the therapy, and the time or interval over which the administration takes place. Thus in some cases, a satisfactory response is observed with less than 6 mg/kg while in other cases more than 800 mg/kg may be indicated. The optimum dosage and the type of administration of the active compounds should of course in each case be determined by a professional expert on the basis of sound judgment and knowledge.

The compounds of the present invention are administered parenterally or orally in any of the usual pharmaceutical forms. These include solid and liquid oral dosage forms such as tablets, capsules, powders, suspensions, solutions, syrups, and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

When used as feedstuff additives, these nitro-β-lactams can be given in admixture with feedstuffs (or with feedstuff preparations) or with the drinking water. The invention therefore includes an animal feedstuff comprising a nutritious material and a compound according to the invention. Examples of suitable nutritious material are oil cake, grain (e.g. barley), fish meal, soya bean meal, exhausted sugar beet chips, silage, hay and skimmed milk.

In this way it is possible to prevent or minimize infection by Gram negative and Gram positive bacteria in the livestock and to achieve better utilization of the feedstuff.

The examples which follow illustrate the preparation of typical compounds according to the invention but are not intended as a limitation. Explanation of abbreviations used: pts. by wt. = parts by weight; pts. by vol. = parts by volume; mins. = minutes; hr. = hour; hrs. = hours; m.p. = melting point; b.p. = boiling point; ethyl acetate = acetic acid ethyl ester; ether = diethyl ether; THF = tetrahydrofuran; abs. = absolute (anhydrous); DMF = dimethylformamide. All yields quoted in % are in % of theory. All temperatures are given in ° C. NMR data are given in ppm in the δ-scale and the terms in parentheses denote: s = singlet; d = doublet; t = triplet; q = quartet. The β-lactam content of the penicillins was determined iodometrically while the β-lactam content of the cephalosporins was determined from the extinction of the β-lactam carbonyl band of the IR-spectrum and from the NMR-spectrum. Some starting materials of Formula II contain varying amounts of water but the anhydrous compounds can be employed equally well. Unless expressly stated otherwise, "ampicillin" denotes the α-aminobenzylpenicillin having the D(—)- = R-configuration in the side-chain. If not specified in the examples, silyl means trimethylsilyl.

EXAMPLE 1

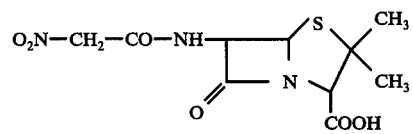

a. 4.0 pts. by wt. of nitroacetic acid chloride in 20 pts. by vol. of abs. methylene chloride were added dropwise while cooling, at temperatures between −20° and −30° C, to a solution of 9.0 parts by weight of silylated (trimethylsilyl) 6-aminopenicillanic acid (prepared according to German Pat. No. 1,159,449) and 2.5 pts. by wt. of triethylamine in abs. methylene chloride. The mixture was stirred for a further hr. and concentrated, the residue was taken up in absolute ether and the triethylammonium chloride was filtered off. 4 pts. by wt. of 6-nitroacetamido-penicillanic acid were precipitated from the filtrate by adding n-propanol.

β-Lactam content: 79%.

b. 59.2 pts. by vol. of 2 N sodium hydroxide solution were added to a suspension of 25.0 pts. by wt. of 6-aminopenicillanic acid in 200 pts. by vol. of a mixture of water and acetone in the ratio of 1:1 (by volume), and the mixture was stirred for 30 minutes. A solution prepared as follows was added dropwise to the above solution at −15° C: 45 pts. by vol. of N-methylmorpholine were added to 11.2 pts. by vol. of chloroformic acid ethyl ester in 150 pts. by vol. of THF at −10° C, the mixture was stirred for 10 mins. and 10 pts. by vol. of concentrated sulphuric acid were added, followed by 20.0 pts. by wt. of the potassium salt of nitroacetic acid in 150 pts. by vol. of THF.

The mixture was stirred for 1 hr. without cooling, the organic solvents were stripped off and the sodium 6-nitroacetamido-penicillinate was isolated (6.5 pts. by wt.).

c. 2.0 pts. by wt. of nitroacetic acid in 50 pts. by vol. of THF were stirred with 2.4 pts. by wt. of N-hydroxysuccinimide and 4.3 pts. by wt, of dicyclohexylcarbodiimide for 1 hr. at 5° C and then for 1 hr. at room temperature. The mixture was concentrated, the residue was taken up in abs. methylene chloride and the dicyclohexylurea (4.0 pts. by wt., corresponding to 85% of theory) was filtered off.

This solution was stirred with 5.1 pts. by wt. of 6-aminopenicillanic acid in 50 pts. by vol. of abs. methylene chloride and 5.8 pts. by vol. of triethylamine for 4 hrs. at 0° C. The mixture was then concentrated, the residue was taken up in water and this mixture was extracted by shaking with ethyl acetate at pH = 7, acidified and again extracted by shaking with ethyl acetate. 6-Nitroacetamido-penicillanic acid was precipitated as the sodium salt by adding an equivalent amount of sodium caprylate solution.

d. 2.0 pts. by wt. of nitroacetic acid in 50 pts. of THF were reacted with 2.8 pts. by wt. of N-hydroxy-benztriazole and 4.3 pts. of dicyclohexylcarbodiimide analogously to Example (c), with 6-aminopenicillanic acid, and the mixture was worked up.

Yield, 7.6 pts. by wt. $C_{10}H_{12}N_3NaO_6S \cdot H_2O$: calculated: C: 35.0, H: 4.1, N: 12.3, S: 9.3; found: C: 34.9, H: 4.6, N: 12.3, S: 8.8. IR (KBr): 1,770, 1,680, 1,600 and 1,560 cm$^{-1}$. NMR (CD$_3$OD): 5.60 (s, 2H), 4.82 (3 replaceable H), 4.35 (s, 1H), 1.68 and 1.58 (s, each of 3H).

The products obtained according to processes b–d were identical.

EXAMPLE 2

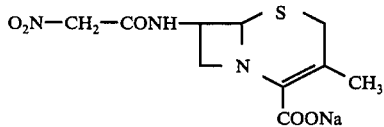

7 pts. by wt. of the dipotassium salt of nitroacetic acid were suspended in 50 pts. by vol. of absolute tetrahydrofurane and 10 pts. by wt. of DMF. After 15 mins. the mixture was cooled to −20° C, 4.2 pts. by wt. of chloroformic acid ethyl ester were added and the mixture was stirred at this temperature for 45 mins. A solution of 9.1 pts. by wt. of 7-amino-3-desacetoxycephalosporanic acid in 200 pts. by vol. of 80% strength aqueous THF, which had been brought to pH 8.2 with triethylamine, was then added dropwise. The mixture was allowed to come to room temperature, stirred for 1 hour and worked up as in Example 5 A)a).

Yield, 88.4% of sodium 7-nitroacetamido-3-methylceph-3-em-4-carboxylate. Decomposition point 130° C. β-Lactam content 65%.

EXAMPLE 3

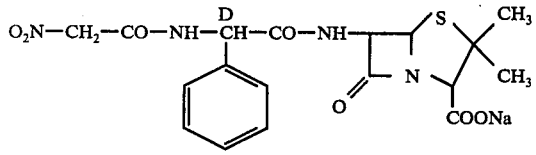

2.4 pts. by wt. of N-hydroxysuccinimide and 4.3 pts. by wt. of dicyclohexylcarbodiimide were added to a solution of 2.0 pts. by wt. of nitroacetic acid ethyl ester in 50 pts. by vol. of THF at 5° C. The solution was kept for 1 hour at 5° C and 1 hour at 20° C and was evaporated, the residue was taken up in 50 pts. by vol. of methylene chloride and the dicyclohexylurea (4.3 pts. by wt. ≙ 91.5%) was filtered off. This solution was added to a solution of 8.2 pts. by wt. of ampicillin in 50 pts. by vol. of abs. methylene chloride and 5.8 pts. by vol. of triethylamine and the mixture was kept overnight at 4° C. It was then concentrated, the residue was taken up in ice water, the mixture was extracted at pH 7 by shaking with ethyl acetate and the aqueous phase was acidified and extracted with ethyl acetate. The latter ethyl acetate phase was dried over magnesium sulphate and the penicillin was precipitated as the sodium salt with the equivalent amount of sodium caprylate.

Yield of sodium 6-[D-α-(nitroacetamido)-phenylacetamido]-penicillanate hemihydrate: 5.6 pts. by wt., having a β-lactam content of 94%.

$C_{18}H_{18}N_3NaO_7S \cdot \frac{1}{2}H_2O$: calculated: C: 46.3, H: 4.3, N: 12.0, S: 6.8; found: C: 46.7, H: 5.2, N: 11.5, S: 6.8. IR (KBr): 1,770, 1,670, 1,600 and 1,560 cm$^{-1}$. NMR (CD$_3$OD): 7.5 (s, 5H), 5.4–5.7 (m, 3H), 4.2 (s, 1H), 1.48 and 1.58 (s, each of 3H).

EXAMPLE 4

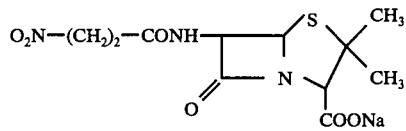

A. 20.5 pts. by wt. of 6-aminopenicillanic acid were suspended in 400 parts by volume of chloroform and dissolved at 0° C by adding 35 pts. by vol. of triethylamine. 11.5 pts. by wt. of 3-nitropropionyl chloride in 60 pts. by vol. of chloroform were added dropwise at −15° C and the mixture was stirred for 30 mins. at −10° C and finally for 30 mins. at room temperature. The chloroform was stripped off, the residue was taken up in water and the mixture was extracted with ethyl acetate. The aqueous phase was cooled to 0° C, brought to pH 2 and extracted repeatedly with ethyl acetate. The ethyl acetate extracts were washed with a little water and dried for 1 hr. over MgSO$_4$. The MgSO$_4$ was filtered off, an equivalent amount of a methanolic sodium caprylate solution was added to the filtrate and the mixture was concentrated. The residue was dissolved in methanol and the solution was added dropwise to a mixture of 5% of methanol in ether, whereupon the sodium salt of 6-(3-nitropropionylamido)-penicillanic acid precipitated; it was dried over P$_2$O$_5$.

Yield of sodium 6-(3-nitropropionylamido)-penicillanate: 38%.

β-Lactam content: 73.4%. IR (KBr): 1,755, 1,655, 1,595, 1,545 and 1,390 cm$^{-1}$. NMR (CD$_3$OD): 5.57 (m 2H), 4.25 (s, 1H), 3.4 and 3.0 (m, each of 2H), 1.70 and 1.50 (s, each of 3H). $C_{11}H_{14}N_3NaO_6S \cdot \frac{1}{4}C_2H_5-O-C_2H_5 \cdot 2H_2O$: calculated: C: 37.55, H: 5.30, N: 10.94, S: 8.35; found: C: 37.5, H: 4.7, N: 10.9, S: 8.4.

B. 3-Nitropropionic acid chloride

3-Nitropropionic acid chloride was prepared by heating 1 pt. by wt. of 2-nitropropionic acid with 1.5 pts. by wt. of thionyl chloride in 3 pts. by wt. of chloroform under reflux until the evolution of gas had ceased. B.p.$_{0.4}$ 70°–75° C.

EXAMPLE 5

A. Sodium 6-(2-nitro-3,3-dimethyl-butyrylamido)-penicillanate

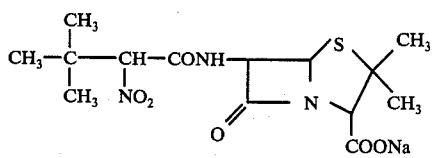

65 pts. by wt. of 6-aminopenicillanic acid were dissolved in 2,000 pts. by vol. of 80 percent strength (by volume) of aqueous THF by adding triethylamine, the mixture was cooled to 0° C and 75 pts. by wt. of 2-nitro-3,3-dimethylbutyric acid chloride were added dropwise. At the same time, the pH value was kept at 7.5 by adding triethylamine. After stirring for 45 mins., the pH was adjusted to 6.5 with dilute hydrochloric acid and the THF was stripped off at room temperature. The aqueous phase was coated with ethyl acetate, brought to pH 1.5 with dilute hydrochloric acid and extracted by shaking twice with ethyl acetate. The ethyl acetate phase was dried over magnesium sulphate and concentrated to 250 pts. by vol., and ether was added, followed by an equivalent amount of sodium caprylate solution, whereupon 25 pts. by wt. of the penicillin precipitated.

β-Lactam content: 95%. IR (KBr): 1,775, 1,680, 1,610 and 1,560 cm⁻¹. NMR (CD₃OD): 5.5 (m, 2H), 5.2 (s, 1H), 4.25 (s, 1H), 1.65 and 1.60 (s, each of 3H). calculated: C: 44.1, H: 5.3, N: 11.0, S: 8.4; found: C: 43.9, H: 5.9, N: 11.5, S: 8.7.

b. 18 pts. by wt. of 6-aminopenicillanic acid trimethylsilyl ester in methylene chloride were reacted with 5 pts. by wt. of triethylamine and 12 pts. by wt. of 2-nitro-3,3-dimethyl-butyric acid chloride overnight at −30° C. Working up takes place as in Example 5(A)(a). The sodium 6-(2-nitro-3,3-dimethyl-butrylamido)-penicillanate had a β-lactam content of 95%.

B. 2-Nitro-3,3-dimethyl-butyric acid chloride.

200 g of 1,1-dichloro-3,3-dimethylbutene-(1) were reacted, analogously to an instruction given by Martynov, Kruglyak and Makarov in J. General Chem. USSR 1963, 3,308–3,318, with 1.2 kg of nitrating acid (HNO₃: H₂SO₄ = 1:9 (by volume)) at 28°–30° C. The organic phase was separated off and distilled in a waterpump vacuum through a 60 cm column surmounted by a rectifying attachment. 53 g of acid chloride of about 60% purity (according to NMR) were obtained. This product was employed directly in the acylation reaction.

EXAMPLE 6

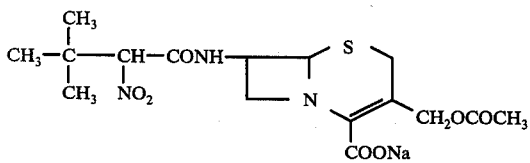

5.4 pts. by wt. of 7-aminocephalosporanic acid were dissolved in 100 pts. by vol. of 80% strength aqueous THF at pH 8 by addition of triethylamine. The solution was cooled to 0° C and 5.0 pts. by wt. of 2-nitro-3,3-dimethylbutyric acid chloride were added dropwise while maintaining the pH value at 7.5 by adding triethylamine. Working up took place as in Example 5 A)a). 3.6 pts. by wt. of sodium 7-(2-nitro-3,3-dimethylbutyrylamido)-3-acetoxymethylceph-3-em-4-carboxylate were obtained.

IR (KBr): 1,770, 1,740, 1,680, 1,605 and 1,570 cm⁻¹. NMR (CD₃OD): 5.6–5.9 and 4.8–5.3 (m, together 4H), 3.2–3.6 (m, 2H), 2.04 (s, 3H), 1.20 and 1.38 (s, together 9H). C₁₆H₂₀N₃NaO₈S.½H₂O: calculated: C: 42.5, H: 4.7, N: 9.3, S: 7.9; found: C: 42.2, H: 4.7, N: 9.3, S: 7.2.

EXAMPLE 7

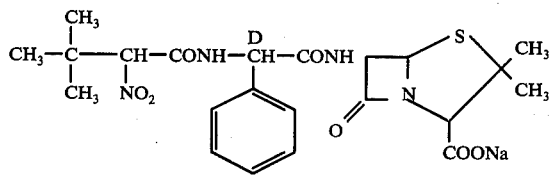

40.4 pts. by wt. of ampicillin were reacted with 20 pts. by wt. of 2-nitro-3,3-dimethyl-butyric acid chloride as in Example 5(A)(a). Yield: 19.5 pts. by wt. of sodium 6-[D-α-(2-nitro-3,3-dimethyl-butyrylamido)-phenylacetamido]-penicillanate of 63% β-lactam content.

IR (KBr): 1,780, 1,675, 1,615 and 1,560 cm⁻¹. NMR (CD₃OD): 7.4 (s, 5H), 5.4–5.7 (m, 3H), 5.27 (s, 1H), 4.17 (s, 1H), 1.50 and 1.55 (s, each of 3H), 1.10 and 1.18 (together 9H).

EXAMPLE 8

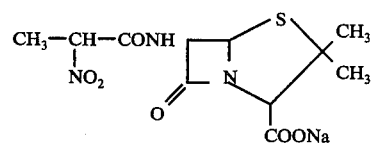

11.0 pts. by wt. of 2-nitropropionyl chloride were reacted with 17.3 pts. by wt. of 6-amino-penicillanic acid as in Example 5(A)(a). Sodium 6-(2-nitropropionylamido)-penicillanate of 73% β-lactam content was obtained.

IR (KBr): 1,770, 1,690, 1,600 and 1,560 cm⁻¹. NMR (D₂O): 5.5–5.7 (m, 2H), 4.3 (s, 1H), 2.1 (s, 3H), 1.53 and 1.60 (s, each of 3H).

C₁₁H₁₄N₃NaO₅S.H₂O: calculated: C: 37.0, H: 4.5, N: 11.8, S: 8.9; found: C: 37.0, H: 5.0, N: 11.6, S: 9.2.

EXAMPLE 9

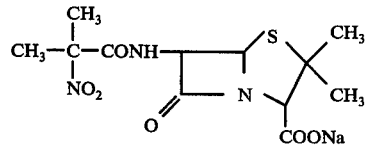

5.8 pts. by wt. of 6-aminopenicillanic acid trimethylsilyl ester and 2.5 pts. by wt. of triethylamine were dissolved in 200 pts. by vol. of abs. methylene chloride and stirred with 6.3 pts. by wt. of 2-nitro-2-methylpropionyl chloride for 1 hr. at −40° C and 1 hr. without cooling. The mixture was concentrated, the residue was taken up in ether and the mixture was filtered and precipitated with n-butanol. 1.8 pts. by wt. of sodium 6-(2-nitro-2-methylpropionylamido)-penicillanate were obtained from the mother liquor by adding sodium caprylate. β-Lactam content: 63%.

IR (KBr): 1,775, 1,685, 1,610 and 1,550 cm⁻¹. NMR (CD₃OD): 5.3–5.6 (m, 2H), 4.3 (s, 1H), 1.8 (s, 6H), 1.58 and 1.68 (s, each of 6H). calculated: C: 40.8, H: 4.6, N: 11.9, S: 9.1; found: C: 41.0, H: 5.8, N: 11.8, S: 10.1.

EXAMPLE 10

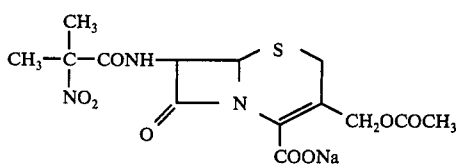

3.2 pts. by wt. of 7-aminocephalosporanic acid trimethylsilyl ester and the equivalent amount of triethylamine were reacted with 4.5 pts. by wt. of 2-nitro-2-methylpropionyl chloride as in Example 9. 2.8 pts. by wt. of sodium 7-(2-nitro-2-methylpropionylamido)-3-acetoxymethylceph-3-em-4-carboxylate were obtained.

IR(KBr): 1,740–1,770 (broad), 1,685, 1,610 and 1,560 cm$^{-1}$.

NMR (CD$_3$OD): 4.8–5.7 (m, 4H), 3.2–3.6 (m, 2H), 2.1 (s, 3H), 1.9 (s, 6H).

EXAMPLE 11

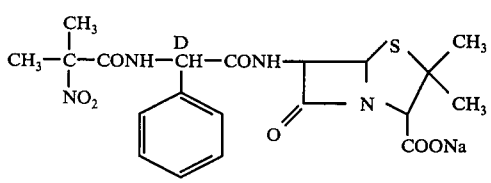

4.0 pts by wt. of ampicillin trimethylsilyl ester were reacted with an equivalent amount of 2-nitro-2-methyl-propionyl chloride in the presence of an equivalent amount of triethylamine, as in Example 9. 1.7 pts. by wt. of sodium 6-[D-α-(2-nitro-2-methyl-propionylamido)-phenylacetamido] penicillanate with a β-lactam content of 86% were obtained.

IR (KBr): 1,775, 1,670, 1,610 and 1,565 cm$^{-1}$.

NMR (CD$_3$OD): 7.4 (s, 5H), 7.65 (s, 1H), 7.5 (q, 2H), 4.22 (s, 1H), 1,83 (s, 6H), 1.50 and 1.58 (s, each of 3H).

C$_{20}$H$_{23}$N$_4$NaO$_7$S.2H$_2$O: calculated: C: 46.1, H: 5.2, N: 10.7, S: 6.2; found: C: 46.6, H: 5.0, N: 9.8; S: 6.2.

EXAMPLE 12

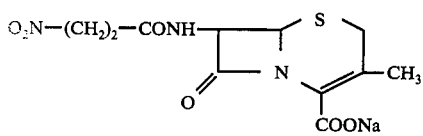

3 pts. by wt. of 7-amino-3-desacetoxycephalosporanic acid were suspended in 50 pts. by vol. of chloroform and 5 pts. by vol. of triethylamine were added at 0° C, whereupon only partial solution occurred. After cooling to −15° C, 1.6 pts. by vol. of chloroform, were added dropwise and the mixture was further processed as in Example 4 A).

0.6 pt. by wt. of sodium 7-(3-nitropropionylamido)-3-methylceph-3-em-4-carboxylate having a lactam content of 70% was obtained.

IR (KBr): 1,740, 1,660, 1,585 and 1,540 cm$^{-1}$.

NMR (CD$_3$OD): 5.6 (m, 2H), 3.2–3.6 (m, 4H), 2.8 (m, 2H), 2.0 (s, 3H).

EXAMPLE 13

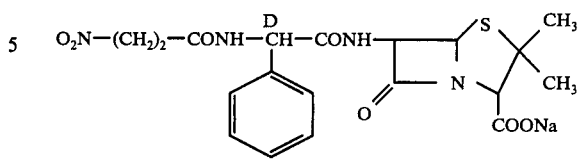

37.8 pts. by wt. of ampicillin trihydrate were suspended in 100 pts. by vol. of methylene chloride, 19 pts. by vol. of triethylamine and 39 pts. by wt. of anhydrous magnesium sulphate were added and the mixture was stirred for 2 hrs. at room temperature. The magnesium sulphate was filtered off, a further 13 pts. by vol. of triethylamine were added, the whole was cooled to −15° C and 11.5 pts. by wt. of 3-nitropropionyl chloride, dissolved in 100 pts. by vol. of methylene chloride, were added dropwise. The reaction mixture was left for 30 mins. at −10° C and 30 mins. at room temperature, the solvent was stripped off and the residue was worked up as in Example 4 A).

Yield, 58.6% of sodium 6-[D-α-(3-nitropropionylamido)-phenylacetamido]-penicillanate.

Decomposition point: 240°–250° C.

β-Lactam content: 96%.

calculated: C: 44.86, H: 4.95, N: 11.02, S: 6.18; found: C: 44.6, H: 5.0, N: 10.9, S: 6.5.

EXAMPLE 14

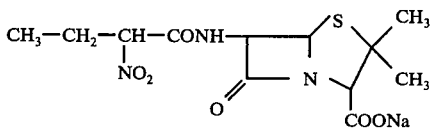

7.2 pts. by wt. of 6-aminopenicillanic acid trimethylsilyl ester and 2.0 pts. by wt. of triethylamine were first introduced into 200 pts. by vol. of abs. methylene chloride and 7.0 pts. by wt. of 2-nitro-butyryl chloride in 50 ml of abs. methylene chloride were added dropwise at −10° C. The mixture was allowed to come to room temperature and was stirred for 2 hrs. and worked up as in Example 9. 12.0 pts. by wt. of sodium 6-(2-nitrobutyrylamido)-penicillanate of 84.6% lactam content were obtained.

IR (KBr): 1,770, 1,680, 1,600 and 1,570 cm$^{-1}$.

NMR (CD$_3$OD+D$_2$O): 5.4–5.7 (m, 2H), 4.25 (s, 1H), 3.39 (q, 2H), 1,60 and 1,68 (s, each of 3H), 1.3 (t, 3H).

EXAMPLE 15

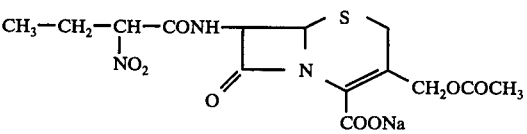

4.2 pts. by wt. of 7-aminocephalosporanic acid trimethylsilyl ester were reacted with 5.0 pts. by wt. of 2-nitrobutyryl chloride as in Example 9.

2.8 g of sodium 7-(2-nitrobutyrylamido)-3-acetoxymethyl-ceph-3-em-4-carboxylate were obtained.

IR (KBr): 1,770, 1,735, 1,690, 1,610 and 1,570 cm$^{-1}$.

NMR (CD$_3$OD): 4.9–5.5 (m, 4H), 3.2–3.6 (m, 4H), 2.05 (s, 3H), 1.3 (t, 3H).

calculated: C: 41.1, H: 4.0, N: 10.3, S: 7.8; found: C: 41.5, H: 5.6, N: 11.1, S: 7.5.

EXAMPLE 16

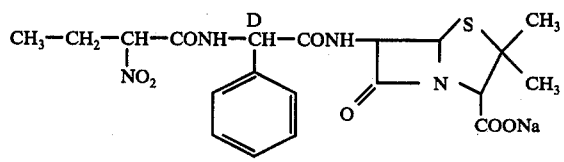

10 pts. by wt. of ampicillin trimethylsilyl ester were reacted with 7 pts. by wt. of 2-nitrobutyryl chloride as in Example 9. 6.5 g of sodium 6-[D-α-(2-nitrobutyrylamido)-phenylacetamido]-penicillanate of 85% β-lactam content were obtained.

IR (KBr): 1,780, 1,680, 1,605 and 1,570 cm$^{-1}$.

NMR (CD$_3$OD): 7.4 (s, 5H), 5.4–5.7 (m, 3H), 4.2 (s, 1H), e.28 (q, 2H), 1.48 s and 1.55 s and 1.30 t (together 9H).

calculated: C: 51.8, H: 5.2, N: 12.0, S: 6.9; found: C: 51.8, H: 6.0, N: 11.4, S: 6.8.

EXAMPLE 17

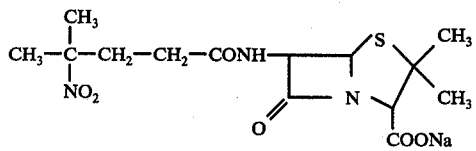

17.9 pts. by wt. of 6-aminopenicillanic acid were suspended in 400 pts. by vol. of 80% strength (by volume) of aqueous THF and triethylamine was added until the pH is 8.3, in the course of which solution occurred. The mixture was cooled to 0° C and 13.5 pts. by wt. of 4-nitro-4-methyl-valeric acid chloride in 35 pts. by wt. of THF were added dropwise, while keeping the pH value at between 7 and 8 by simultaneous addition of triethylamine. When no further triethylamine was consumed, 150 pts. by wt. of water were added, the THF was stripped off and the residue was worked up as described in Example 4 A). Sodium 6-(4-nitro-4-methyl-valeroylamido)-penicillanate was obtained in a yield of 68%.

Decomposition point: 170° C.
β-Lactam content: 71.6%.
IR (KBr): 1,770, 1,660, 1,610 and 1,535 cm$^{-1}$.
C$_{14}$H$_{20}$N$_3$NaO$_6$S.H$_2$O
calculated: C: 42.10, H: 5.56, N: 10.53, S: 8.04; found: C: 42.1, H: 5.8, N: 10.0, S: 8.1.

EXAMPLE 18

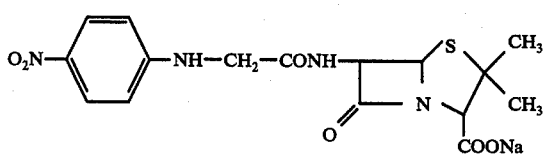

3.9 pts. by wt. of N-(4-nitrophenyl)-glycine were suspended in 50 pts. by vol. of absolute THF, 2.0 pts. by wt. of triethylamine were added at 0° C and the mixture was stirred until dissolved (about 10 mins.) and cooled to −15° C. After adding 2.2 pts. by wt. of chloroformic acid ethyl ester and 2 drops of N-methylmorpholine, the mixture was stirred for 30 mins. at the same temperature, a solution of 4.8 pts. by wt. of 6-aminopenicillanic acid in 100 pts. by vol. of 80% strength (by volume) aqueous THF, which were brought to pH 8.3 with triethylamine, was added and the whole was stirred for 1 hr. at room temperature. Working up took place as in Example 4 (A).

Sodium 6-(4-nitrophenylamino-acetamido)-penicillanate was obtained in a yield of 88.5%.

Decomposition point: 210°–214° C.
β-Lactam content: 74.7%.
IR (KBr): 1,760, 1,665 and 1,600 cm$^{-1}$.
NMR (CD$_3$OD): 8.08 (d, 2H), 6.70 (d, 2H), 5.56 (pseudo-s, 2H), 4.21 (s, 1H), 4.02 (s, 2H), 1.54 (s, 6H).
C$_{16}$H$_{17}$N$_4$NaO$_6$S.2H$_2$O: calculated: C: 42.48, H: 4.67, N: 12.36, S: 7,09; found: C: 43.0, H: 4.6, N: 12.0, S: 6.7.

EXAMPLE 19

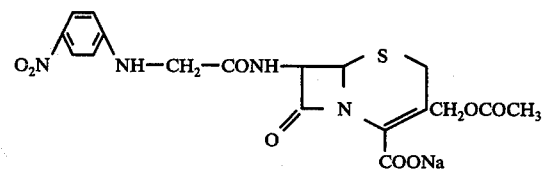

2.2 pts. by wt. of N-(4-nitrophenyl)-glycine and 3.0 pts. by wt. of 7-aminocephalosporanic acid were reacted as in Example 18. 3.8 pts. by wt. of sodium 7-(4-nitrophenylamino-acetamido)-3-acetoxymethyl-ceph-3-em-4-carboxylate of 75% β-lactam content were obtained.

IR (KBr): 1,755, 1,680 and 1,600 cm$^{-1}$;
NMR (CD$_3$OD): 8.08 (d, 2H), 6.70 (d, 2H), 5.75 (d, 1H), 5.05 (d, 1H) with superposed (m, 2H), 4.05 (s, 2H), 3.6 (m, 2H), 2.05 (s, 3H).

EXAMPLE 20

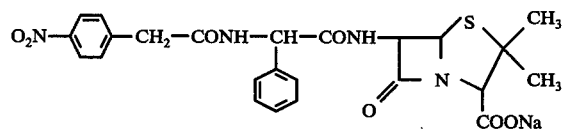

9.3 pts. by wt. of ampicillin trihydrate, 6.9 pts. by vol. of triethylamine and 4.2 pts. by wt. of 4-nitrophenylacetyl chloride were reacted as in Example 13.

2.6 pts. by wt. of sodium 6-[D-α-(4-nitrophenylacetamido)-phenylacetamido]-penicillanate of 80% β-lactam content were obtained.

IR (KBr): 1,765, 1,660, 1,600 and 1,510 cm$^{-1}$.
NMR (CD$_3$OD): 8.20 (d, 2H), 7.55 (d, 2H), 5.65 (s, 1H), 5.45 (q, 2H), 4.17 (s, 1H), 3.77 (s, 2H), 1.60 and 1.53 (s, each of 3H).

EXAMPLE 21

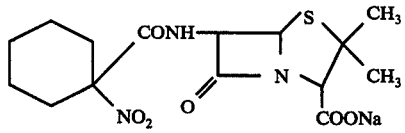

7.2 pts. by wt. of 6-aminopenicillanic acid trimethylsilyl ester and 8.0 pts. by wt. of 1-chlorocarbonyl-1-nitrocyclohexane were reacted as in Example 9.

4.7 pts. by wt. of sodium 6-(1-nitrocyclohex-1-ylcarbamido)-penicillanate of 92% β-lactam content were obtained.

IR (KBr): 1,770, 1,675, 1,610 and 1,560 cm$^{-1}$.

NMR (CD$_3$OD): 5.3–5.6 (m, 2H), 4.25 (s, 1H), 2.2–2.5 (m, 4H), 1.53 s and 1.65 s with superposed m of total 12 H.

calculated: C: 45.8, H: 5.1, N: 10.7, S: 8.2; found: C: 45.8, H: 6.6, N: 10.6, S: 8.7.

EXAMPLE 22

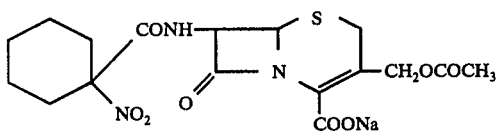

8.3 pts. by wt. of 7-aminocephalosporanic acid trimethylsilyl ester and 8.0 pts. by wt. of 1-chlorocarbonyl-1-nitro-cyclohexane were reacted as in Example 9. Sodium 7-(1-nitrocyclohex-1-ylcarbamido)-3-acetoxymethylceph-3-em-4-carboxylate were thus obtained.

IR (KBr) : 1,730–1,770 (broad), 1,680, 1,610 and 1,550.

NMR (CD$_3$OD): 4.8–5.5 (m, 4H), 3.2–3.6 (m, 2H), 2.05 (s, 3H), 2.2–2.4 (m, 4H), 1.4–1.7 (m, 6H).

What is claimed is:

1. A compound selected from the group consisting of a nitro-β-lactam of the formula:

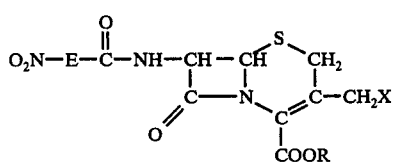

wherein

O$_2$N—E is nitroalkyl of 1 to 6 carbon atoms;
R is hydrogen or

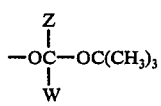

in which each of Z and W is independently hydrogen or lower alkyl; and X is hydrogen, hydroxy, acetoxy, carbamoyl, and the pharmaceutically acceptable salts of said lactams in which R is hydrogen.

2. A compound according to claim 1 wherein R is hydrogen and X is hydrogen or acetoxy.

3. A compound according to claim 1 which is a salt of said nitro-β-lactam in which R is hydrogen, said salt being selected from the group consisting of the sodium, potassium, magnesium, calcium, aluminium, di-(lower alkyl)-amine, tri-(lower alkyl)amine, procaine, dibenzylamine, N,N'-dibenzylethylenediamine, N-benzyl-β-phenylethylamine, N-methylmorpholine, N-ethylmorpholine, 1-ephenamine, dehydroabietylamine, N,N'-bis-dehydroabietylethylenediamine and N-(lower alkyl)-piperidine salts.

4. A compound according to claim 1 which is 7-nitroacetamido-3-methylceph-3-em-4-carboxylic acid or the sodium salt thereof.

5. A compound according to claim 1 which is 7-(2-nitro-3,3-dimethylbutyrylamido)-3-acetoxymethylceph-3-em-4-carboxylic acid or the sodium salt thereof.

6. A compound according to claim 1 which is 7-(2-nitro-2-methylpropionylamido)-3-acetoxymethylceph-3-em-4-carboxylic acid or the sodium salt thereof.

7. A compound according to claim 1 which is 7-(3-nitropropionylamido)-3-methylceph-3-em-4-carboxylic acid or the sodium salt thereof.

8. A compound according to claim 1 which is 7-(2-nitrobutyrylamido)-3-acetoxymethylceph-3-em-4-carboxylic acid or the sodium salt thereof.

9. A pharmaceutical composition comprising an antibacterially effective amount of a compound according to claim 1 in combination with a pharmaceutical carrier.

10. The method of combatting bacterial infections in an animal or human which comprises administering to said animal or human an antibacterially effective amount of a compound according to claim 1.

11. A composition for promoting growth in animals which comprises a growth promoting effective amount of a compound according to claim 1 in combination with a nutritious carrier or animal drinking water.

12. The method of promoting growth in an animal which comprises administering to said animal a growth promoting effective amount of a compound according to claim 1.

13. A compound according to claim 1 wherein X is hydrogen, hydroxy or acetoxy.

* * * * *